(12) United States Patent
Gregg et al.

(10) Patent No.: US 11,497,641 B2
(45) Date of Patent: Nov. 15, 2022

(54) LOWER LIMB POWERED ORTHOSIS WITH LOW RATIO ACTUATION

(71) Applicant: Board of Regents, The University of Texas System, Austin, TX (US)

(72) Inventors: Robert D. Gregg, Austin, TX (US); Hanqi Zhu, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 667 days.

(21) Appl. No.: 15/977,154

(22) Filed: May 11, 2018

(65) Prior Publication Data

US 2018/0325713 A1 Nov. 15, 2018

Related U.S. Application Data

(60) Provisional application No. 62/504,826, filed on May 11, 2017.

(51) Int. Cl.
*A61F 5/01* (2006.01)
*A61H 3/00* (2006.01)
(Continued)

(52) U.S. Cl.
CPC .......... *A61F 5/0102* (2013.01); *A61F 5/0123* (2013.01); *A61F 5/0127* (2013.01); *A61H 1/024* (2013.01); *A61H 1/0237* (2013.01); *A61H 1/0262* (2013.01); *A61H 1/0266* (2013.01); *A61H 3/00* (2013.01); *B25J 9/0006* (2013.01); *A61F 2002/6836* (2013.01); *A61F 2002/701* (2013.01); *A61F 2005/0139* (2013.01); *A61F 2005/0155* (2013.01); *A61H 2003/007* (2013.01); *A61H 2201/0176* (2013.01); *A61H 2201/1207* (2013.01); *A61H 2201/1215* (2013.01); *A61H 2201/1472* (2013.01);
(Continued)

(58) Field of Classification Search
CPC .... A61F 5/0105; A61F 5/0125; A61F 5/0102; A61F 2005/0139; A61H 3/00
See application file for complete search history.

(56) References Cited

U.S. PATENT DOCUMENTS 10,265,195 B2 * 4/2019 Mooney ................. A61H 1/024
2014/0364962 A1 * 12/2014 Gregg ................... A61F 2/6607
623/24

(Continued)

OTHER PUBLICATIONS

Design and Validation of a Torque Dense, Highly Backdrivable Powered Knee-Ankle Orthosis, Zhu et al, May 1, 2017, IEEE International Conference on Robotics and Automation (Year: 2017).*

*Primary Examiner* — David H Willse

(57) ABSTRACT

The present disclosure is relates to an orthosis device. The orthosis device, in one embodiment, includes an actuator housing, and an electric motor coupled to the actuator housing, the electric motor including a motor stator and a motor rotor, and the electric motor further having high output torque. The orthosis device, in this embodiment, further includes a low-ratio transmission coupled to the actuator housing, the transmission including a gear system coupled to the actuator housing, and a drive system coupling the electric motor and the gear system, wherein a combination of the electric motor and transmission provide a user backdrivable orthosis device.

20 Claims, 18 Drawing Sheets

(51) Int. Cl.
*A61F 2/70* (2006.01)
*A61H 1/02* (2006.01)
*B25J 9/00* (2006.01)
*A61F 2/68* (2006.01)

(52) U.S. Cl.
CPC .. *A61H 2201/164* (2013.01); *A61H 2201/165* (2013.01); *A61H 2201/50* (2013.01); *A61H 2201/5007* (2013.01); *A61H 2201/5058* (2013.01); *A61H 2201/5061* (2013.01); *A61H 2205/106* (2013.01)

(56) References Cited

U.S. PATENT DOCUMENTS

2018/0296422 A1* 10/2018 Sawicki ................ F16H 19/005
2020/0347919 A1* 11/2020 Lee ........................... F16H 3/66

* cited by examiner

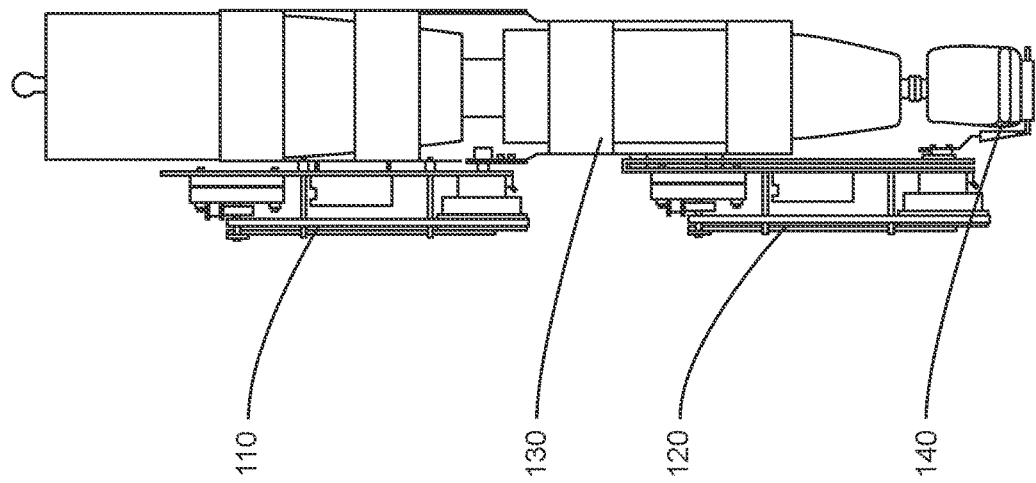
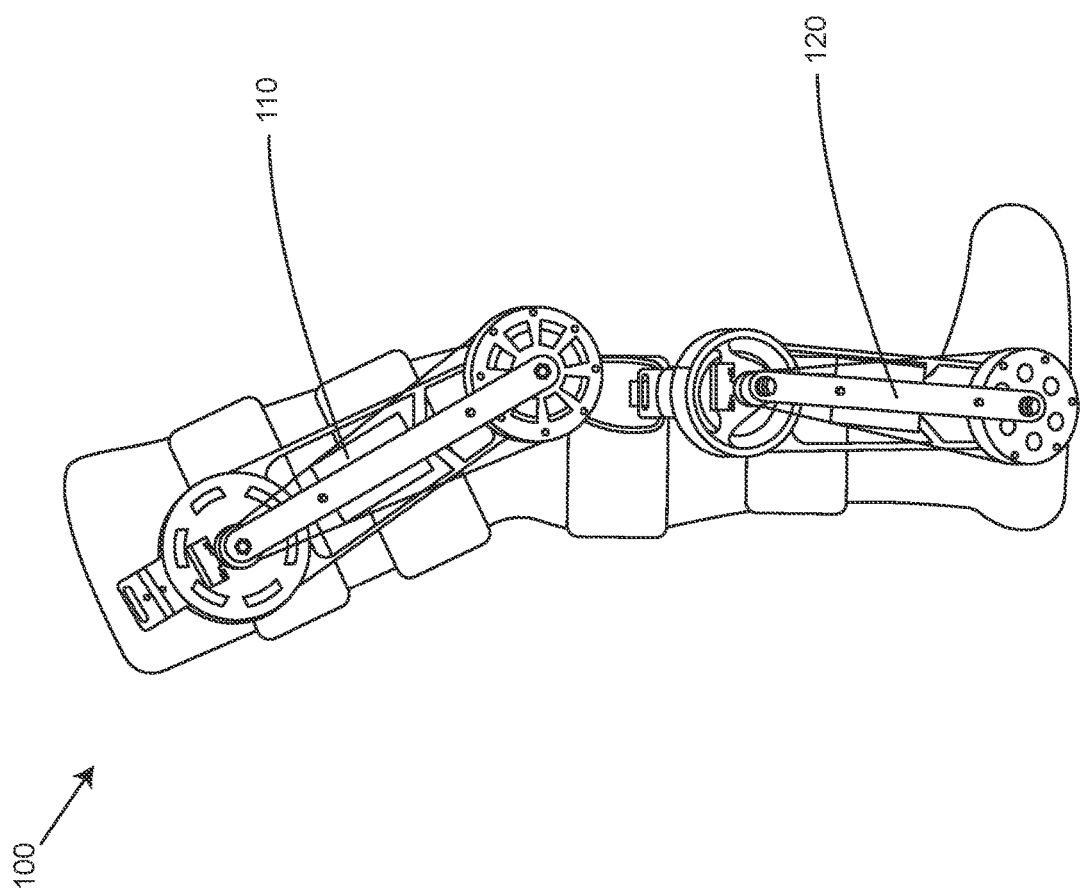
FIG. 1

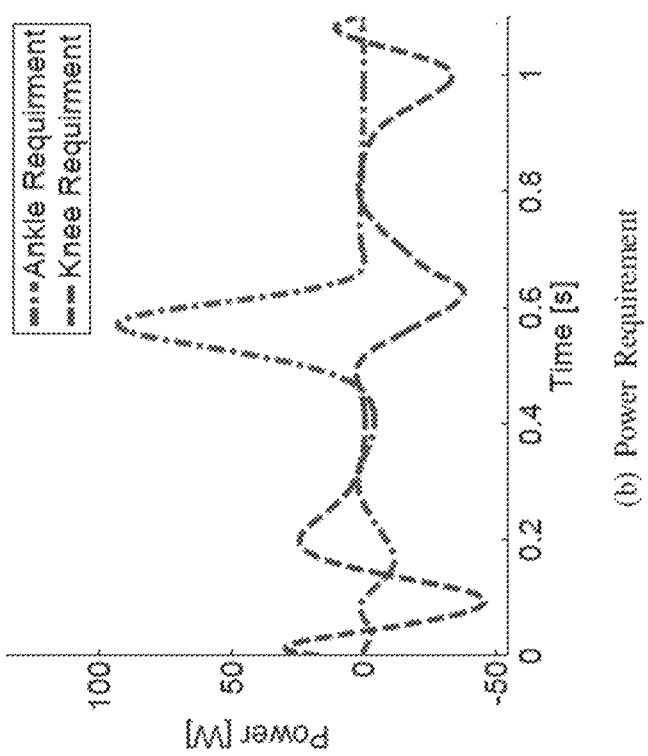
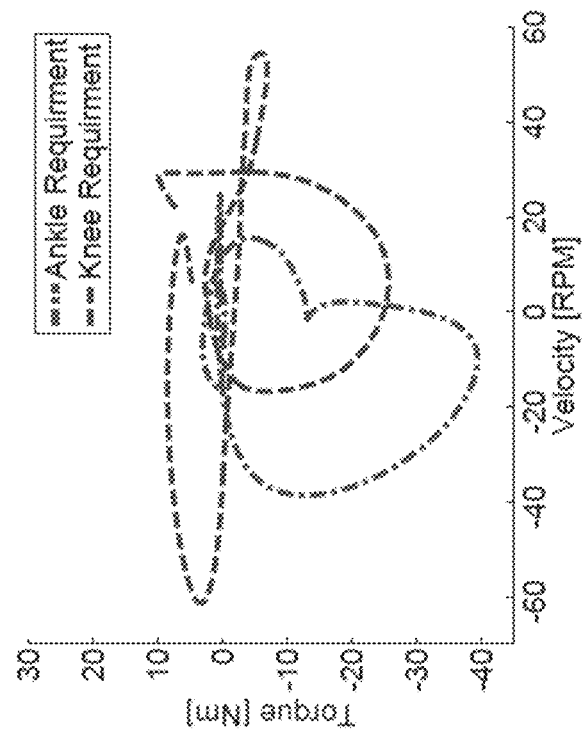
Fig. 3

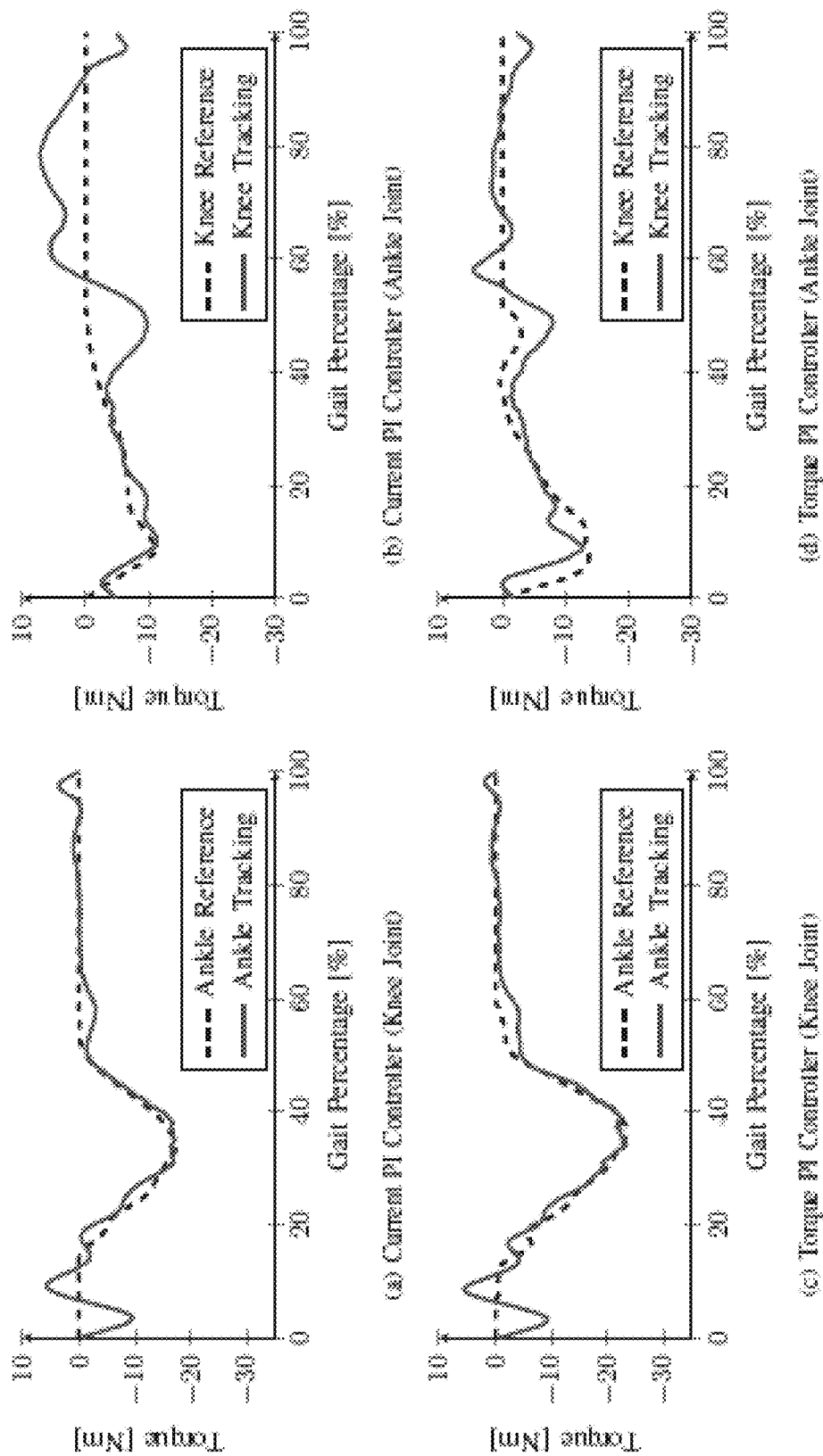
Figs. 10a-d

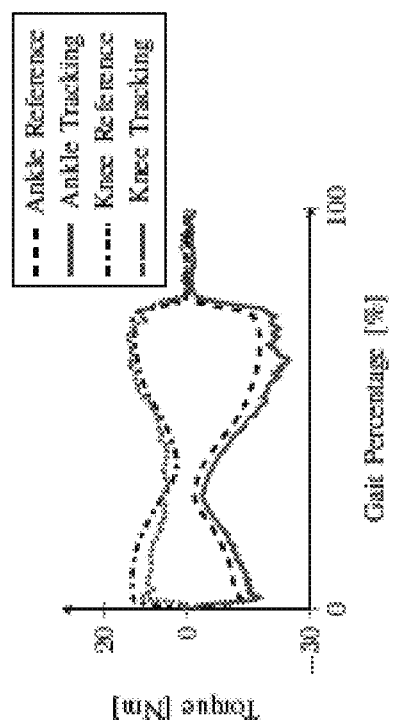
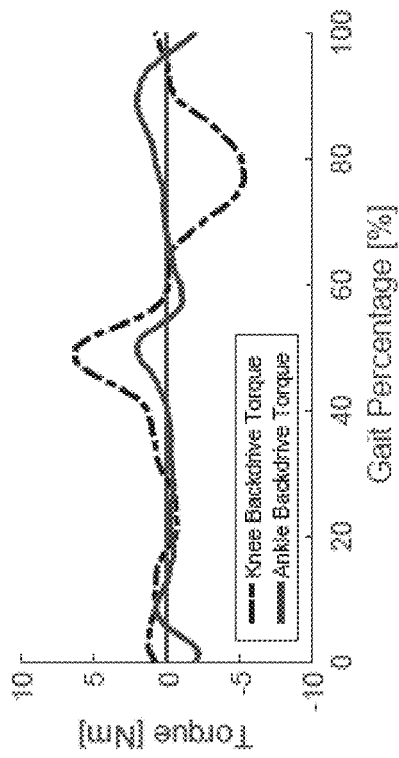
Figs. 11a & b

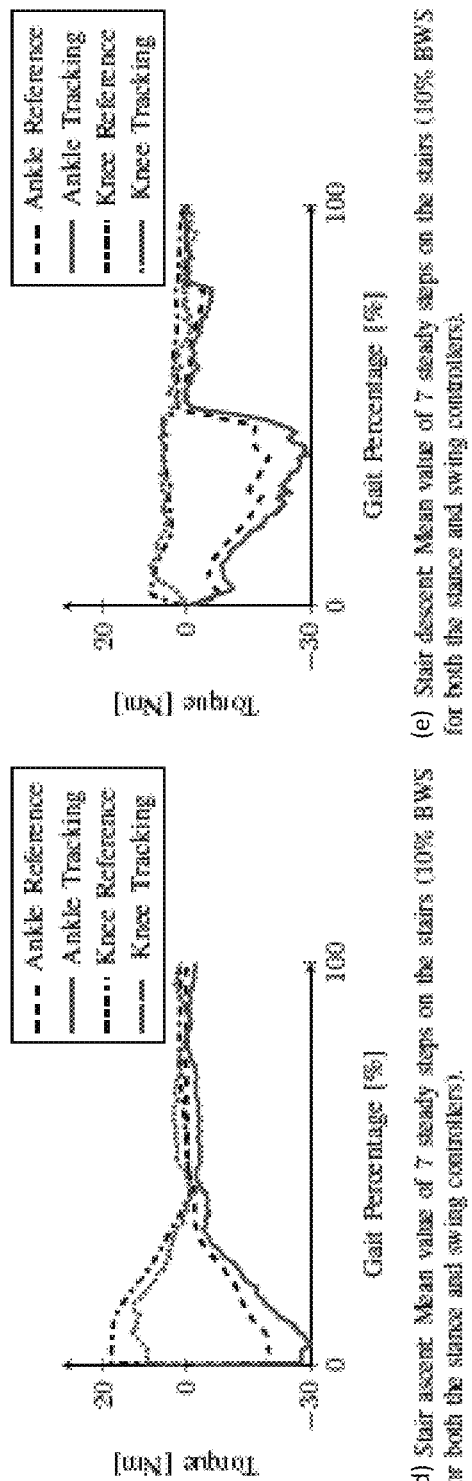
Figs. 11d & e

Fig. 13. Results from the static high torque test. The output torque is measured by the FUTEK torque sensor. A 3 Nm preload torque is added to eliminate the mechanical backlash from the test platform Fig. 15 Measured DC-link current from regeneration test. The DC-link current is measured by a current probe (TCPA 300, Tektronix, Inc.) and recorded by oscilloscope (DPO 3024B, Tektronix, Inc.).

ic="US 11,497,641 B2"

LOWER LIMB POWERED ORTHOSIS WITH LOW RATIO ACTUATION

CROSS-REFERENCE TO RELATED APPLICATION

This application claims the benefit of U.S. Provisional Application Ser. No. 62/504,826, filed on May 11, 2017, entitled "LOWER LIMB POWERED ORTHOSIS WITH LOW RATIO ACTUATION," commonly assigned with this application and incorporated herein by reference.

GOVERNMENT LICENSE RIGHTS

This invention was made with government support under HD080349 awarded by the National Institutes of Health. The government has certain rights in this invention.

TECHNICAL FIELD

This application is directed, in general, to limb powered orthoses and, more specifically, to limb powered orthoses that are easily backdrivable.

BACKGROUND

Physical training is often needed for patients to relearn how to walk after a stroke. However, finite medical resources limit the frequency and availability of physical training. To address this, researchers are investigating powered lower-limb rehabilitation orthoses to relieve the repetitive and physically tasking duties of therapists, as well as to improve patient recovery efficacy. Currently, most lower-limb rehabilitation orthoses are stationary and only available in a small number of hospitals, due to high cost and large size. Personal mobile lower-limb orthoses that can be used in the clinic or at home are desirable for different rehabilitation purposes.

BRIEF DESCRIPTION

Reference is now made to the following descriptions taken in conjunction with the accompanying drawings, in which:

FIG. 1 is an orthosis system;

FIG. 3 illustrates the requirements of one embodiment of the disclosed orthosis system;

FIG. 4b illustrates a section view of the actuator illustrated in FIG. 4a;

FIGS. 10a-10d illustrate the torque outputs of normal walking;

FIGS. 11a-11e illustrate the measured torque from multiple task experiments;

DETAILED DESCRIPTION

Figure 2:
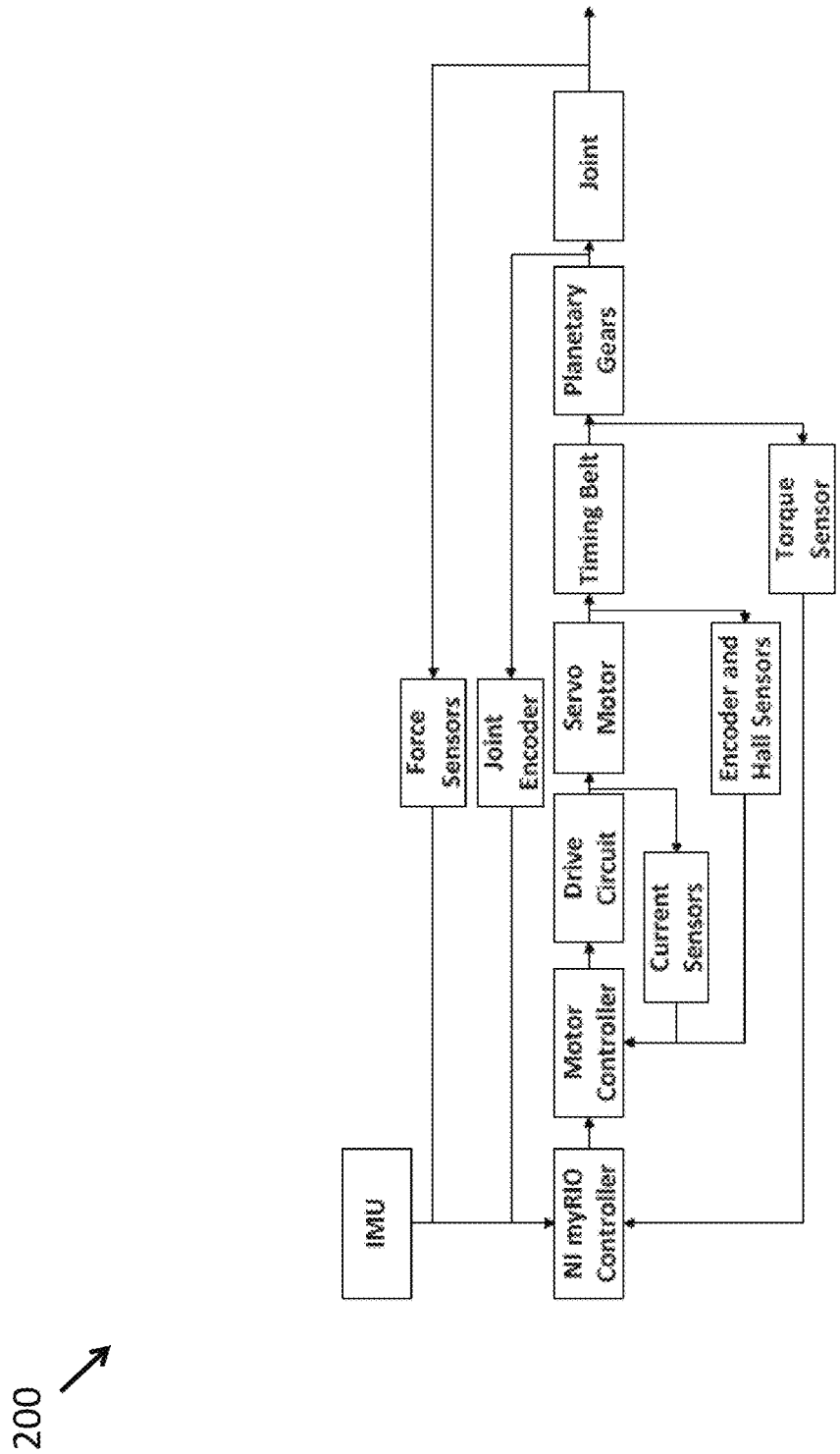
FIG. 2 is a schematic of one embodiment of an orthosis system in accordance with the disclosure.

Due to the high torque requirements of lower-limb joints, past research has focused on increasing the torque density of powered orthoses to provide enough output torque within an acceptable weight. Consequently, the combination of a high-speed motor and a high-ratio transmission, e.g., ball screw or harmonic drive, is common in traditional powered lower-limb orthoses. The present disclosure has recognized that the use of a high-ratio transmission results in high mechanical impedance, which means that the user cannot move their joints without help from the orthosis.

An orthosis is said to be backdrivable if users can drive their joints without a high resistive torque from the orthosis. Backdrivability may not be necessary for patients who cannot contribute to their walking gait, e.g., patients with spinal cord injuries. However, for patients who still have some control of their legs, a backdrivable orthosis can promote user participation and provide comfort during physical therapy. In particular, a mobile powered lower-limb orthosis for stroke rehabilitation purposes should be as mechanically transparent as possible.

In addition, advanced torque control methods for emerging physical therapies require the orthosis to accurately control its torque output during locomotion. Series Elastic Actuators (SEA) have been widely researched and applied in mobile orthoses to address the above two requirements: backdrivability and torque control. In particular, a torque control system can be implemented by measuring the displacement of elastic components. Active (e.g., as opposed to intrinsic) backdrivability can then be achieved by servoing the spring displacement to zero. However, current orthoses with SEA suffer from various limitations, such as low output torque, complex system architecture, bulky size, excessive manufacturing cost or limited force/torque control bandwidth.

The present disclosure, for the first time, details the design of a novel powered limb (e.g., knee-ankle) orthosis that achieves 1) high output torque with a low-ratio transmission (e.g., without a high-ratio transmission) and 2) precise torque control and backdrivability without series elastic components.

For the purpose of the present disclosure and claims, a high output torque motor has a peak output torque (e.g., measured over a 10 second time period) of at least about 1.0 Nm. Similarly, for the purpose of the present disclosure and claims, a very high output torque motor has a peak output torque (e.g., measured over a 10 second time period) of at least about 1.5 Nm, and an extremely high output torque motor has a peak output torque (e.g., measured over a 10 second time period) of at least about 2.0 Nm. Also, for the purpose of the present disclosure and claims, an excessively high output torque motor has a peak output torque (e.g., measured over a 10 second time period) of at least about 4.0 Nm.

For the purpose of the present disclosure and claims, a high torque density motor has a torque density (e.g., a measure of the peak torque output divided by the motor's stator and rotor weight) of at least about 3.3 Nm/kg. Similarly, for the purpose of the present disclosure and claims, a very high torque density motor has a torque density (e.g., a measure of the peak torque output divided by the motor's stator and rotor weight) of at least about 5.0 Nm/kg, and an extremely high torque density motor has a torque density (e.g., a measure of the peak torque output divided by the motor's stator and rotor weight) of at least about 6.7 Nm/kg. Also, for the purpose of the present disclosure and claims, an excessively high torque density motor has a torque density (e.g., a measure of the peak torque output divided by the motor's stator and rotor weight) of at least about 13.3 Nm/kg.

Additionally, for the purpose of the present disclosure and claims, a low-ratio transmission is a transmission with a ratio of 32:1 or less. Similarly, for the purpose of the present disclosure and claims, a very low-ratio transmission is a transmission with a ratio of 24:1 or less, and an extremely low-ratio transmission is a transmission with a ratio of 16:1 or less. Additionally, for the purpose of the present disclosure and claims, an excessively low-ratio transmission is a transmission with a ratio of 12:1 or less.

Similarly, for the purpose of the present disclosure and claims, a device that is user backdrivable is a device wherein its static torque (e.g., minimum backdrive torque to begin motion of the motor shaft) is less than about 20 Nm. Likewise, for the purpose of the present disclosure and claims, a device that is very user backdrivable is a device wherein its static torque (e.g., minimum backdrive torque to begin motion of the motor shaft) is less than about 5 Nm, and a device that is extremely user backdrivable is a device wherein its static torque (e.g., minimum backdrive torque to begin motion of the motor shaft) is less than about 2.5 Nm. Also, for the purpose of the present disclosure and claims, a device that is excessively backdrivable is a device wherein its static torque (e.g., minimum backdrive torque to begin motion of the motor shaft) is less than about 2.0 Nm.

Precise torque control is extremely helpful to a device manufactured according to the present disclosure, in that accurate position, velocity and straight up torque can be calculated. To eliminate the need for a high-ratio transmission, the presented orthosis uniquely uses a high torque density electrical motor. A distributed low-ratio transmission is designed to reduce the mechanical impedance and allow the user to easily move their joints. The compact, lightweight actuator provides enough torque and power output to assist the joints during human locomotion. In particular, in one example embodiment the orthosis can achieve a continuous output torque of 30 Nm (and 60 Nm peak torque) at each joint during normal use (e.g., walking speeds when the orthosis is coupled to the knee-ankle). The orthosis can be extremely light. For instance, in one particular embodiment each actuation system (e.g., including the actuator housing, electric motor, and transmission that includes the gear system and drive system) might weigh less than about 1.2 kg and thus have a higher torque density than previous low-ratio orthosis actuators. In one embodiment, a closed-loop torque control system with a reaction torque sensor can precisely achieve assistive or resistive torques for different physical therapies.

While the present disclosure has recognized, for the first time, that high torque output and backdrivability are typically considered tradeoffs in wearable robots, the presented orthosis successfully balances the core requirements of rehabilitation training: backdrivability, torque control, high torque density, and light weight. Moreover, a device according to the present disclosure is capable of achieving high torque output during stance phase and low backdrive torque during swing phase, without using a clutch or variable transmission. Thus, instead of increasing the ratio of the transmission as in previous designs, the presented orthosis achieves a high output torque by increasing the torque density of the electrical motor. The present disclosure demonstrates that the core requirements of a powered orthosis can be met with a nearly direct drive actuation system, which has several advantages in the context of legged locomotion. In particular, the custom low-ratio transmission of the disclosed orthosis provides intrinsic backdrivability without the cost and complexity of variable transmissions, clutches, and/or series elastic components.

The design of one embodiment of a powered (e.g., unilateral) lower-limb orthosis, including the actuation system, electrical system, and torque control system will now be described and illustrated. A rendering of one embodiment of the overall system 100 is shown in FIG. 1. The ankle and knee are actuated to dynamically offload body weight from the affected leg. In this embodiment, the two actuator modules (e.g., knee actuator module 110 and ankle actuator module 120) are attached to a knee-ankle-foot orthotic brace 130 to drive the knee and ankle joints. In the disclosed embodiment, torque is transferred to the human ankle through a shoe insert 140 (e.g., carbon fiber shoe insert in one embodiment). Furthermore, several sensors may be installed on the brace and the actuator modules to monitor key variables of the gait cycle.

Turning to FIG. 2, illustrated is one embodiment of a block diagram 200 for the whole orthosis system. As shown in the embodiment of FIG. 2, a servo motor generates a torque, which is then amplified by a timing belt and a planetary gear transmission.

To provide a sufficient torque output for gait training, the actuation system is designed, in one embodiment, to generate about 30% of the torque and power of healthy human joints during level-ground walking. While 30% has been selected in this embodiment, other embodiments exist wherein the actuation system is designed to generate anywhere from about 10% to about 90% of the torque and power of healthy human joints. Notwithstanding, one embodiment of the targeted requirements is shown in FIG. 3. To avoid using a high-ratio transmission, it is desirable for the motor to generate higher torque. In the embodiment at hand, a high torque density PMSM (e.g., AC servo motor) is used to provide sufficient input torque and power to the transmission. By optimizing the motor winding configuration, the custom motor (which may be purchased as MF0096008 from Allied Motion, Inc.) can produce about 2.4 Nm peak torque and about 200 W power. In this example embodiment, the PMSM has distributed windings to reduce the torque ripple and produce a smoother torque output.

Figure 4A:
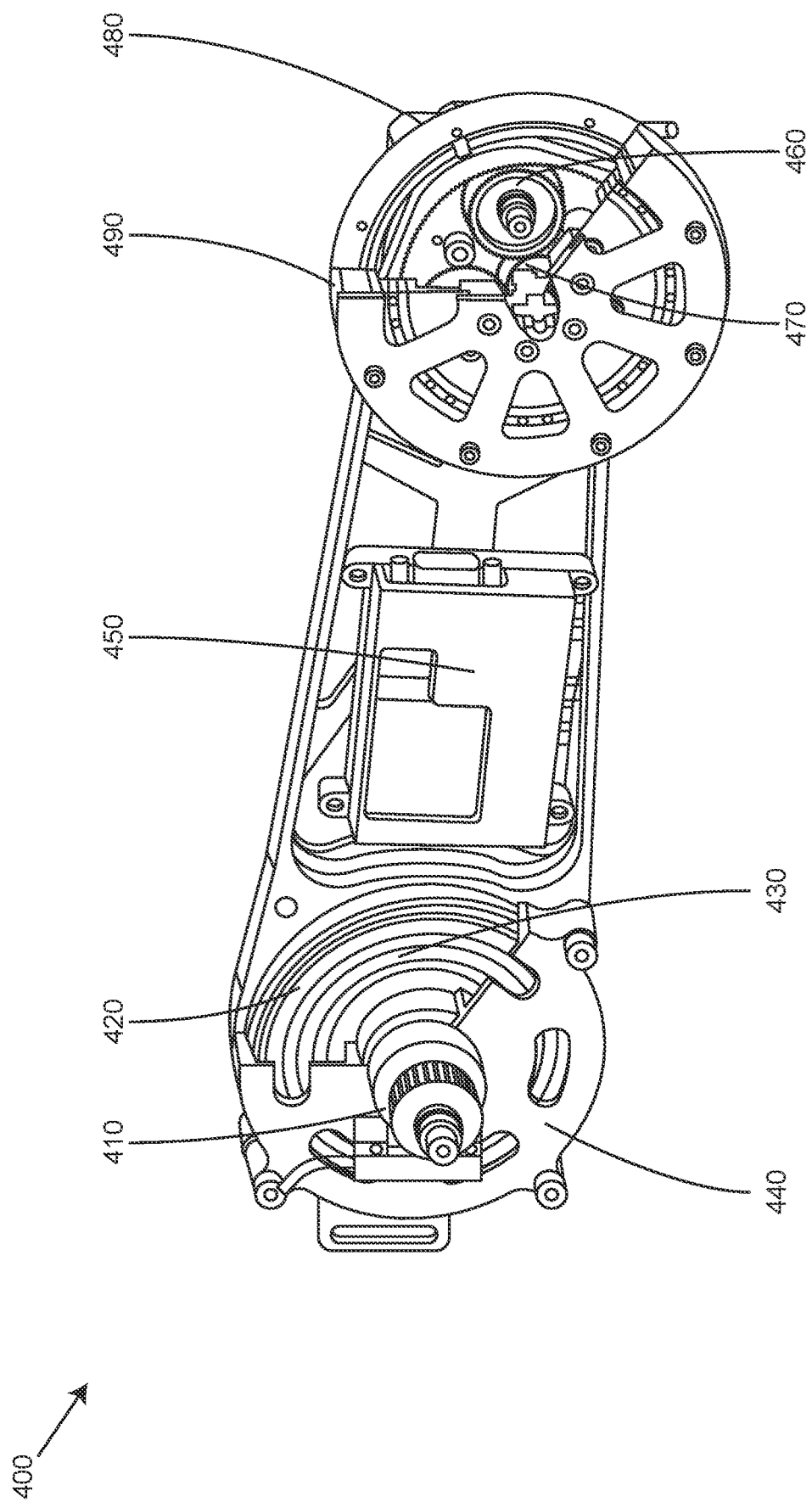
FIG. 4a illustrates a schematic of one embodiment of an actuator.
Figure 4B:
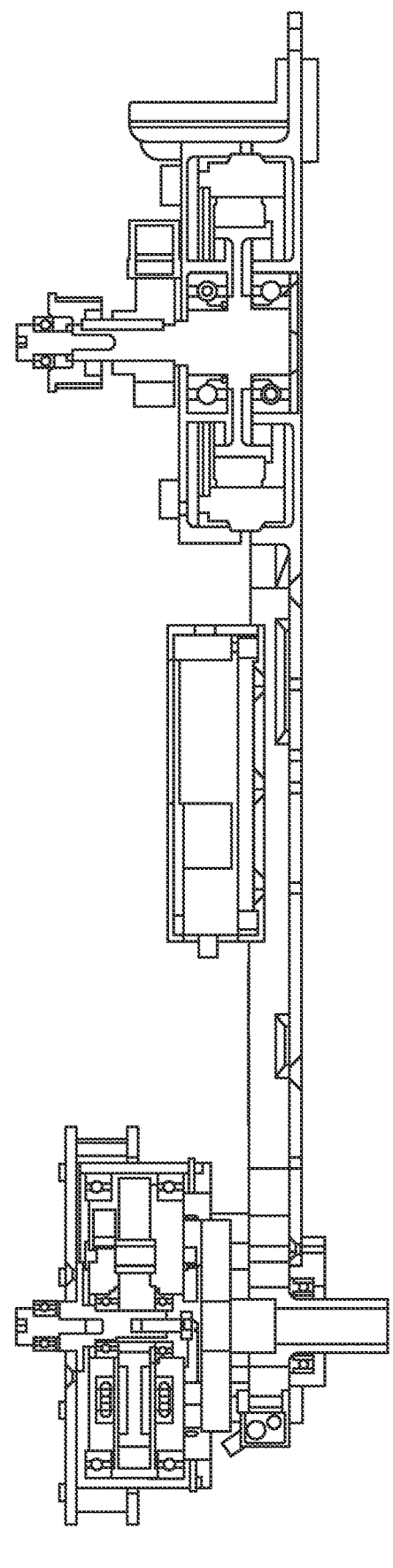

In accordance with one aspect of the disclosure, a distributed two-stage low-ratio transmission is designed for the actuator. A poly chain GT carbon timing belt (3MR, ratio 4:1, Gates Industry, Inc.—or other timing belt) may be used to amplify the motor torque and to move the actuator weight closer to the user's center of mass. Unique to the present disclosure, this may be used to minimize the metabolic burden of added weight during locomotion. In one embodiment, a custom 6:1 planetary gear transmission is built inside the driven sprocket of the timing belt to minimize weight and size. The overall ratio of the two-stage transmission, in one embodiment is 24:1 with an estimated efficiency of 90%. A schematic of the actuator 400 is shown in FIG. 4*a*. A section view of the actuator 400 is shown in FIG. 4*b*. The actuator, in the embodiment of FIGS. 4*a* and 4b, includes a motor encoder 410, a motor stator 420, a motor rotor 430, housing 440 (e.g., PMSM housing), an actuator driver 450, a planetary gear 460, sun gear 470, ring gear 480 and driven sprocket 490. As one skilled in the art appreciates, the actuator 400 may include additional features neither shown or described and remain within the scope of the disclosure.

This embodiment of the actuator design achieves the required torque output by increasing the torque density of the electrical motor rather than the ratio of the transmission. Using the low-ratio transmission dramatically reduces the reflected inertia. Consequently, intrinsic backdrivability is achieved without much (e.g., any in one embodiment) sensing or control. The combination of the torque dense motor and the distributed low-ratio transmission can produce, in one embodiment, approximately 156 Nm output torque in theory. However, the motor's torque is limited by a thermal condition, and the motor's velocity output is limited by working voltage. To balance the torque and velocity requirements, in the embodiment shown, the actuation system is designed to provide about 30 Nm continuous torque output with peak velocity 80 RPM. The motor driver's maximum current (e.g., 30 A in one embodiment) and the mechanical structure limit the peak actuator torque to about 60 Nm.

The mechanical structure of the actuation system is mainly manufactured with aluminum alloy, but other lightweight materials are within the purview of the disclosure. Several carbon fiber mechanical pieces, in certain embodiments, are used to reduce heavy metal material and enhance the strength of the actuation system. In the embodiment shown, with the use of a frameless motor and a custom transmission, all core components are integrally designed with the mechanical structure to further reduce the weight of the orthosis. For instance, the motor housing is part of the main structure of the orthosis in the embodiment shown. The final weight of each actuation system (e.g., including the actuator housing, electric motor, and transmission that includes the gear system and drive system), in the design illustrated above, is less than about 2.0 kg, and in one embodiment less than about 1.2 kg. Thus, in this embodiment, the total weight of the orthosis is approximately 4.6 kg.

Figure 5:
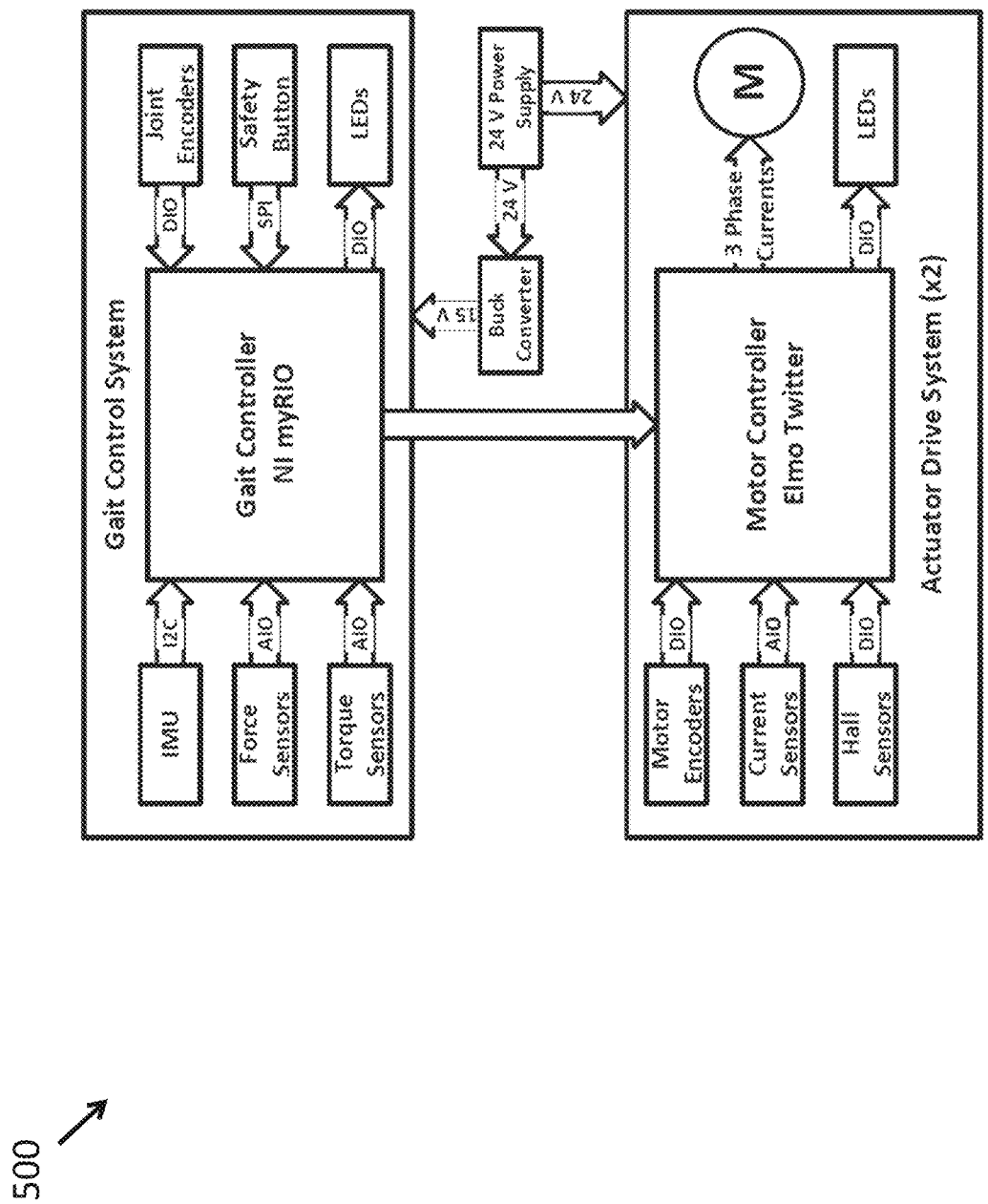
FIG. 5 is a block diagram of one exemplary electrical system.

The electrical system of the lower-limb orthosis, in the illustrated embodiment, has two main parts: a high-level gait control system and a low-level actuator drive system. The gait control system monitors the key variables of the user's gait to implement any given torque-based rehabilitation algorithm. The actuator drive system drives the actuator to track torque commands from the gait control system. The block diagram of the electrical system 500 is shown in FIG. 5.

The gait control algorithm is implemented on a myRIO 1900 microcontroller (e.g., as might be purchased from National Instruments, Inc.), which has a dual-core ARM microprocessor and a Xilinx FPGA. To achieve different torque based rehabilitation control algorithms, several features from the user's gait cycle (e.g., gait phases and joint angles) are measured by the following sensors. The phase of gait, e.g., stance vs. swing, may be detected with two force-sensing resistors (e.g., the FlexiForce A301, as may be purchased from Tekscan, Inc.) embedded into a flexible insole, which may be placed beneath the user's foot in their shoe. These two force sensors may be placed along the normal path of the center of pressure, with one under the heel and the other under the ball of the foot. A Connex 350 3D printer may print the insole from a rubber-like polyjet photopolymer. Two magnetic incremental encoders (6400 CPR, LM13, Renishaw, Inc.), which may be located at the output shaft of the actuator, measure the ankle and knee angles. The components and I/O channels of the high-level gait control system are integrated through a custom Printed Circuit Board (PCB).

The actuator drive system, in one embodiment, is designed to precisely control each actuator. The PMSM may be driven by a field oriented motor controller (e.g., such as the G-TWI-25/100-SE, which may be purchased from Elmo Motion Control, Ltd.). This motor controller may have faster response time and less torque ripple compared to a trapezoidal motor control. Three hall-effect sensors (e.g., such as SS461A, which may be purchased from Honeywell, Inc.) and a magnetic incremental encoder (e.g., such as the 6400 CPR, LM13, which may be purchased from Renishaw, Inc.) may be attached to the motor to obtain accurate absolute position feedback for the field oriented motor controller. A reaction torque sensor (e.g., M2210E, which may be purchased from Sunrise Instruments Co., Ltd.) may be installed at the output shaft of the actuator to measure the real torque output from the actuator. A custom low-level PCB for each joint may be used to integrate the I/O signals from sensors and motor drivers and communicates with the high-level PCB through a cable (e.g., HD-15 cable).

A common method for torque control is based on estimating the actuator's output torque through the motor phase currents and the transmission ratio and efficiency. The electromagnetic motor torque $T_e$ and actuator output torque $T_a$ are given by the following equation:

$$T_a = T_e \cdot \tau \cdot \eta = (3P/2) \cdot \lambda_m \cdot I_q \cdot \tau \cdot \eta, \quad (1)$$

where P is the number of motor poles, $\lambda_m$ is the motor flux linkage, $I_q$ is the active current in the d-q rotating reference frame, $\eta$ is the transmission efficiency, and $\tau$ is the transmission ratio. Equation (1) determines the reference motor current to achieve the desired output torque, and the reference motor current is regulated by a proportional-integral (PI) control loop around the motor driver (the inner loop in FIG. 5).

Unfortunately, the transmission efficiency $\eta$ is not constant during dynamic motion. As a result, if the actuator's output torque is estimated only from the motor phase current, a resultant torque error will occur. In order to accurately track the torques commanded from the gait control system, a second (outer) torque control loop is implemented to compensate the torque error measured by the reaction torque sensor. Both loops (inner current loop and outer torque loop) use proportional-integral (PI) control to enforce the commanded torque.

Figure 6:
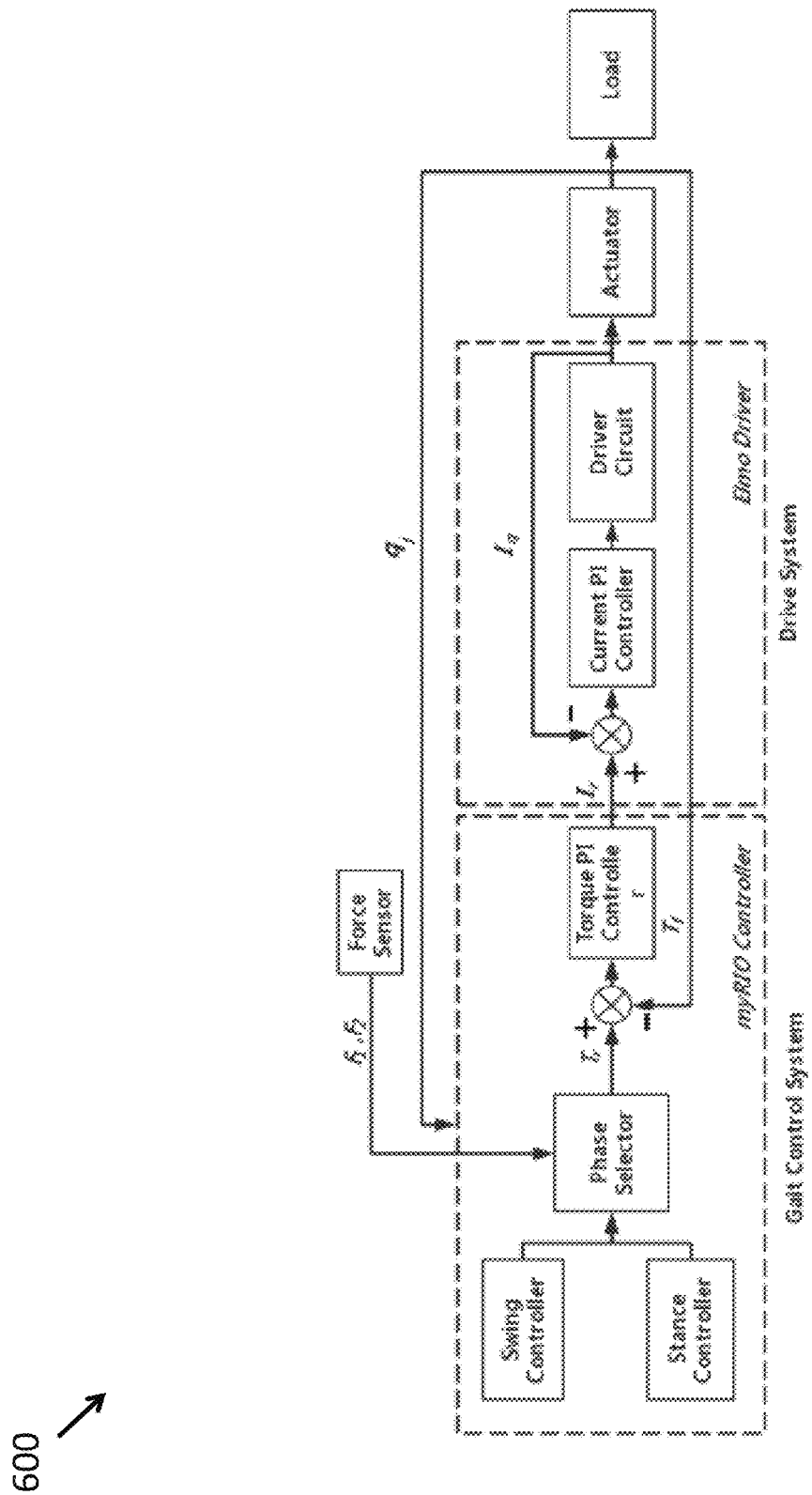
FIG. 6 is a torque control system schematic in accordance with the disclosure.

One embodiment of a control schematic 600 is shown in FIG. 6. In the torque control system schematic illustrated in FIG. 6, $\theta_j$ represents joint angles, $F_1$ and $F_2$ are ground reaction forces, $T_r$ is torque reference, $T_f$ is actuator torque output feedback, $I_r$ is current reference, and $I_q$ is motor active current. The phase selector detects the stance and swing phase. The stance and swing controllers produce the torque reference. The actuator drive system contains two closed-loop PI controllers. The inner loop is the current PI controller, which controls the motor's current. The outer loop is the torque PI controller to compensate for the actuator's torque error. Additionally details of a control system that may be used with the present disclosure may be found in Application No. PCT/US2016/065558 entitled "Torque Control Methods for Powered Orthosis", filed on or about Dec. 8, 2016, which is based upon U.S. Provisional Application No. 62/266,959 entitled "Torque Control Methods for Powered Orthosis", filed on or about Dec. 14, 2015, both of which are incorporated herein by reference, and filed herewith.

Figure 7:
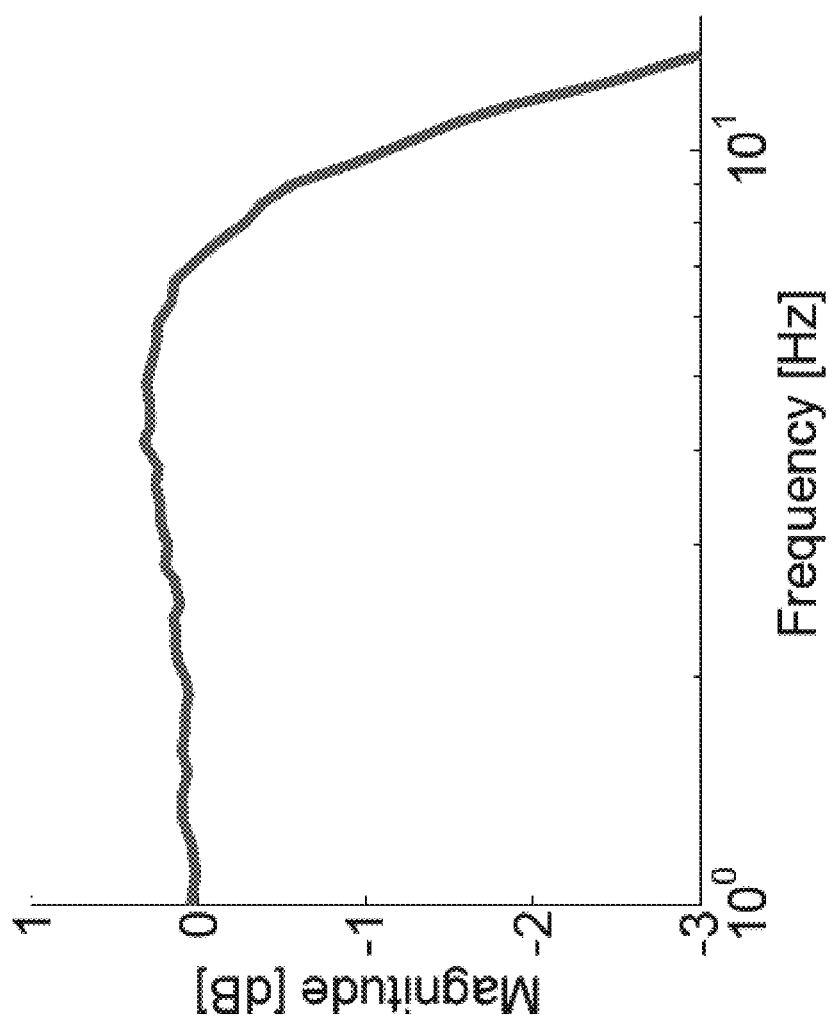
FIG. 7 illustrates the magnitude of the velocity closed-loop bandwidth.

Before experimenting with human subjects, a closed-loop velocity bandwidth test of the actuation system's dynamic performance was performed. Although the control objective may vary between different rehabilitation algorithms, actuator velocity is an important variable to evaluate system dynamic performance. In the closed-loop velocity bandwidth test, the motor was controlled by field-oriented control over various frequencies, and the actuator's output velocity was recorded. A simple PD velocity control loop was implemented through the motor controller. During this long experiment time, the motor was limited to its continuous working current of 10 A for safety reasons. The target velocity of the bandwidth test was set to 1000 RPM, which is a normal operating velocity during walking. The experiment results in FIG. 7 illustrate that the actuator's bandwidth frequency was about 12 Hz, which is higher than that required for normal human walking (4-8 Hz). FIG. 7 illustrates that the frequency at about −3 dB is about 12 Hz, which shows that the presented orthosis has sufficiently fast dynamic performance for gait assistance.

The orthosis design was validated in two experiments with a healthy human subject wearing the orthosis while walking on a treadmill. A passive walking test (i.e., zero command torque) was conducted to demonstrate both intrinsic and active backdrivability. A high torque-walking test (using a high-level quasi-stiffness controller) then demonstrated the output torque and power capabilities of the orthosis.

Figure 8:
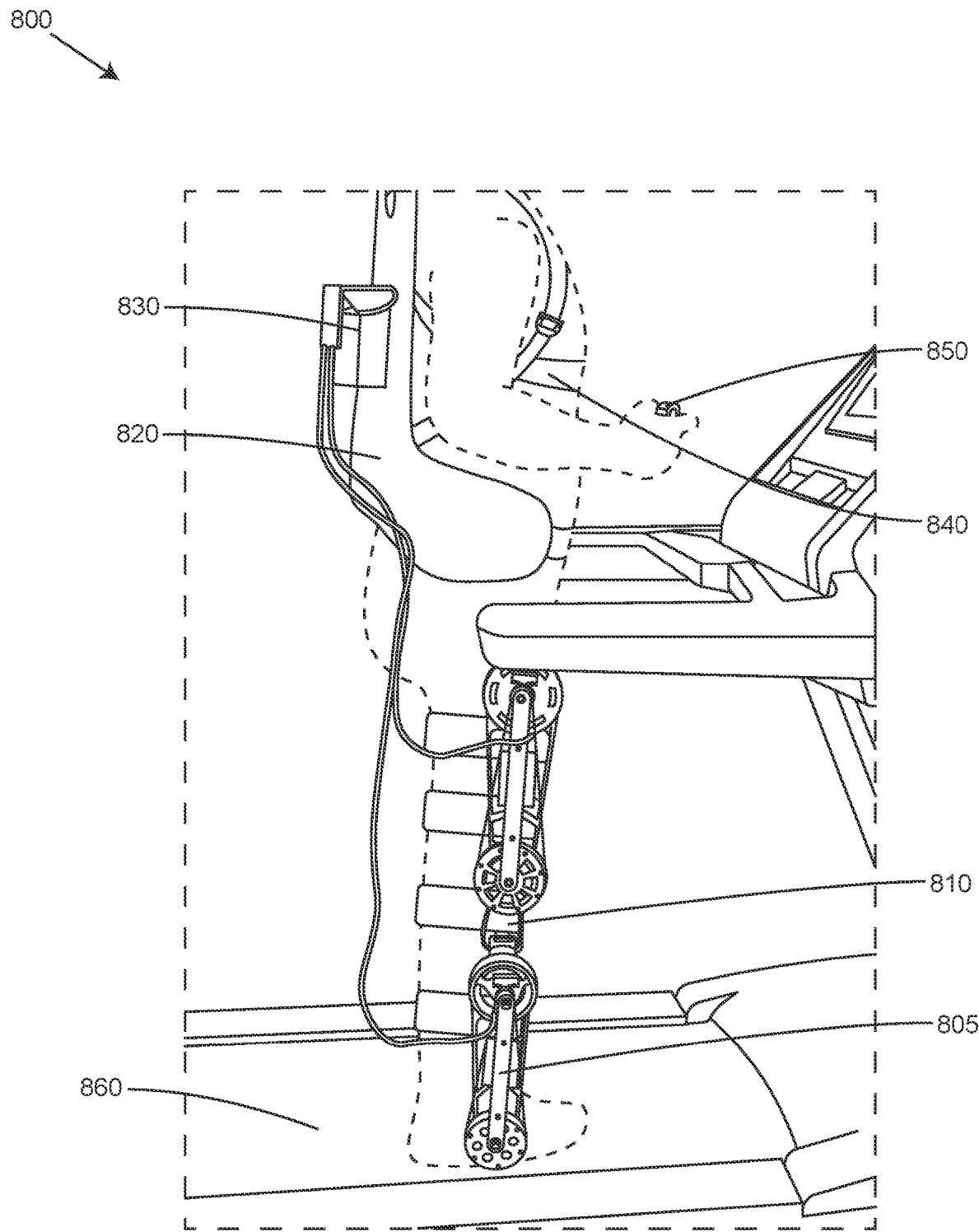
FIG. 8 illustrates a human subject experiment setup.

The experimental setup 800 is shown in FIG. 8. The orthosis 805 was attached to a knee brace 810 and tightened with four flexible straps around the subject's right leg. The subject wore a back brace 820, which carried the gait control system 830. A strap connected the orthosis and the back brace to help suspend the weight of the orthosis.

A safety harness 840 was attached to the subject's torso to prevent falling. Additionally, a safety button 850 was held in the subject's hand during the experiments. If the button were to be released, the actuation drive system would be deactivated.

Passive and high torque walking tests were conducted with this experimental setup. The treadmill 860 speed was set to 2.0 miles per hour (MPH) for passive walking test and 2.7 MPH for high torque tests, which is faster than a stroke patient's normal walking speed. The faster walking speed was chosen to examine dynamic backdrive conditions and to demonstrate the high power capabilities of the device. Data was recorded once the subject reached a steady gait (after about 5 steps).

Figure 9:
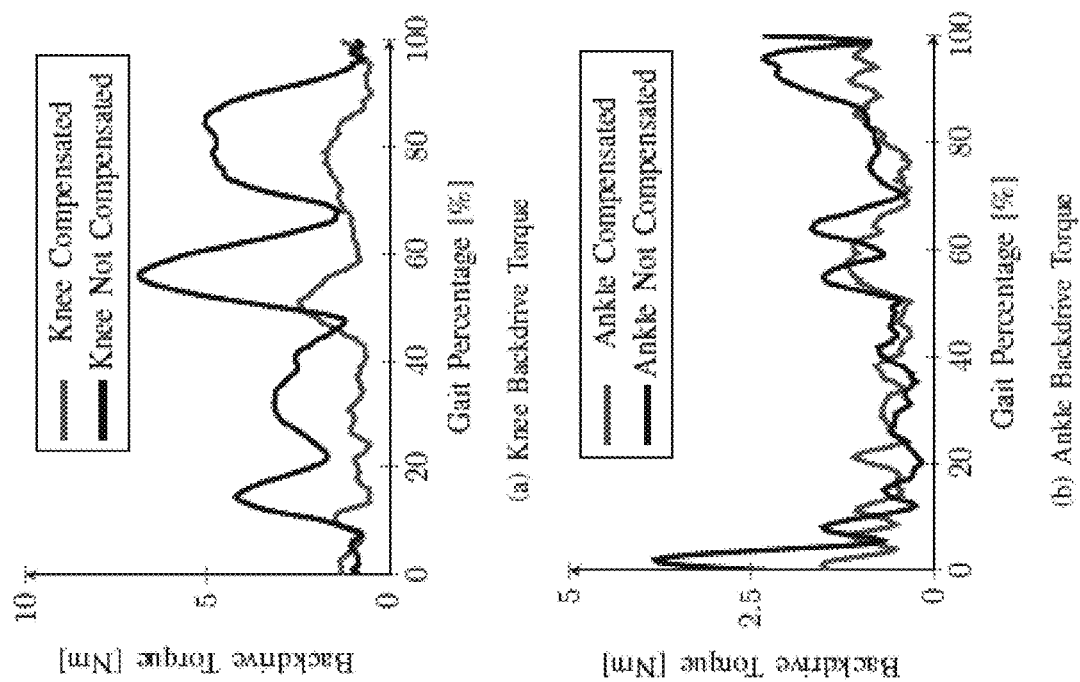
FIG. 9 illustrates backdrive compensation with fast passive walking.
Figure 11C:
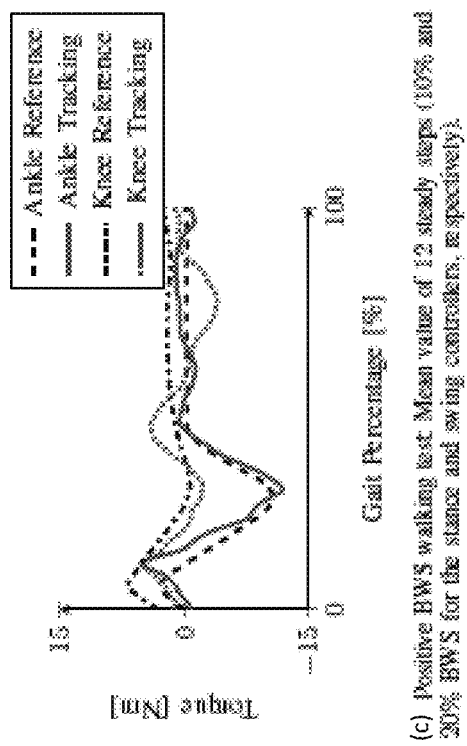

The command torque for both joints was set to zero for the passive walking test. The subject began this test with active torque compensation enabled, e.g., using the double-closed-loop torque controller. After several steps, the user released the safety button and deactivated the actuator. The torque sensor, located at the actuator's output shaft, measured the torque between the human and the orthosis during walking on the treadmill. The measured backdrive torque during passive walking is shown in FIG. 9. Each curve was calculated by the average absolute value of 10 normal walking steps before and after the button releasing moment.

The amplitudes of the dynamic backdrive torques were lower than about 8 Nm. The peak dynamic backdrive torque of the ankle joint occurred during early stance, primarily due to heel contact. The ankle's dynamic backdrive torque during swing was only about 2.5 Nm. The dynamic backdrive torques would likely be smaller in a clinical application, where slower walking speeds are expected. Additionally, the static backdrive torque for the example embodiment has been measured at about 2.5 Nm, thereby providing an extremely backdrivable device.

By using the double-closed-loop torque controller, the backdrive torques were further reduced. The mean value of the average absolute torque was reduced by about 23% for the ankle joint and 63% for the knee joint. The peak backdrive torque was reduced by 58% for the ankle joint and 64% for the knee joint. Aside from the actuation system, misalignment of the orthosis brace and heel contact contributed to the remaining backdrive torque.

A high torque walking test aimed to validate the output torque and power capabilities of the orthosis. Quasi-Stiffness Control was adopted as an example control strategy, which implements a virtual spring at each joint based on the slope of the desired torque-angle curve for healthy human walking. Quasi-stiffness directly maps the measured joint angle to the command torque, providing a simple high-level controller for high torque testing. Quasi-stiffness determined the command torque during the stance period, whereas the reference torque was set to zero during swing to further validate backdrivability. To simplify implementation, the average of the knee quasi-stiffness values of the stance phase for the knee joint was adopted. Two different ankle quasi-stiffness values were used for the ankle joint. The control law is given by If stance $$u_{knee} = \alpha K_k \theta_k,$$

$$u_{ankle} = \begin{cases} \alpha K_{a1} \theta_a & \text{if } \theta_a \leq \overline{\theta} \\ \alpha K_{a2} \theta_a & \text{if } \theta_a > \overline{\theta} \end{cases}$$

If swing $$u_{knee} = u_{ankle} = 0,$$

where $U_{knee}$ and $U_{ankle}$ denote the torque being applied at the knee and ankle joints, $\alpha=0.3$ denotes the 30% support ratio, $\theta_a$ and $\theta_k$ denote the relative angles for the ankle and knee joints, and $K_k=6.29$ Nm·deg$^{-1}$ is the quasi-stiffness value for the knee joint. An angular threshold $\theta$ was manually tuned to trigger the transition from ankle dorsi-flexion with $K_{a1}=6.53$ Nm·deg$^{-1}$ to plantar-flexion with $K_{a2}=21.16$ Nm·deg$^{-1}$. The stance and swing transitions were detected using two force sensors located at the heel and toe part of the shoe insert. The ankle plantar-flexion and knee flexion were defined as the positive angular directions. To guarantee safety and smooth transitions, a fading process was applied when switching between phases, e.g., using the weighted sum of the stance and swing torque laws.

Two different low-level actuator drive modes were employed with this high-level control strategy. The current control mode used the inner current loop in FIG. 6 to control the actuator torque output. The second mode used the double-closed-loop torque controller in FIG. 6 to compensate the measured torque error. The parameters of the torque PI controller were manually tuned to minimize backdrive torque, whereas the current PI parameters were tuned to minimize response time. The ankle's torque reference was set to zero at the beginning of each stance phase to avoid vibration from heel contact.

Before beginning the high torque test, the feedback for the two force sensors was calibrated for detecting the transitions between stance and swing. The angle feedback for all joints was initialized while the subject stood in an upright position. The mean and variance over 10 steady steps with both low-level actuator drive modes are shown in FIG. 10.

The torque controller tracked the torque reference well during both the stance and swing phases. Current Control Mode tracked the torque reference accurately during stance phase, and had a relatively large torque error during swing phase, which is shown in FIG. 10(*a*) and FIG. 10(*b*). The low-ratio transmission allowed for a nearly linear torque constant between the motor current and the actuator output torque. This allowed the current controller to estimate the actuator torque output accurately during stance phase. The torque error of the current controller during swing phase was mainly caused by the intrinsic backdrive torque. The performance of the current controller demonstrates the potential to implement a torque control system without using a torque sensor.

Figure 12:
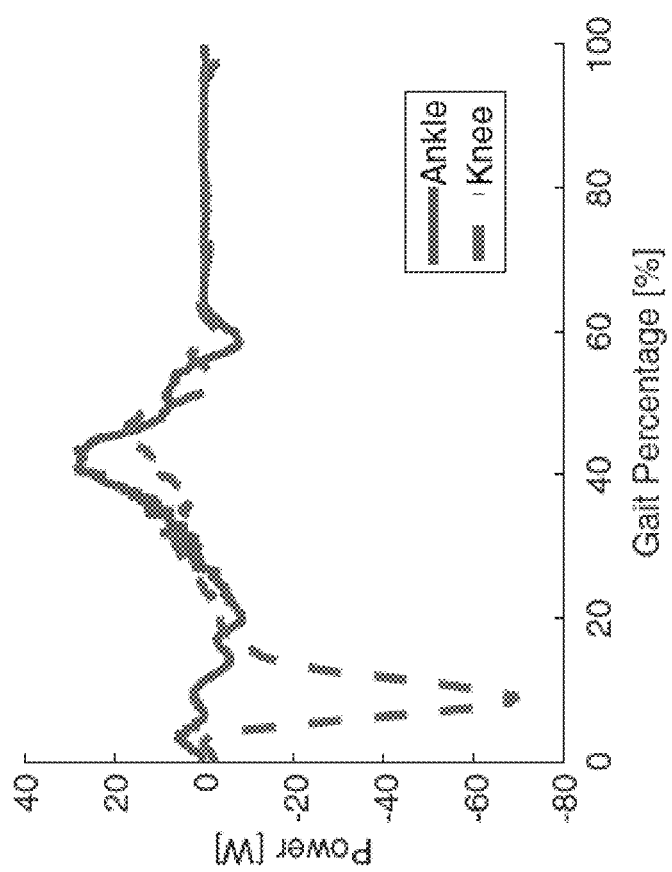
FIG. 12 illustrates the power output of normal walking with torque PI controller.

FIGS. 11*a*-11*e* illustrate the measured torque from multiple task experiments. The average power output with the double-closed-loop torque controller is shown in FIG. 12.

The peak ankle power was lower than expected during late stance. By comparing with the passive walking case, it was found that ankle dorsiflexion during early stance was reduced by the high extension torque command of the quasi-stiffness controller. The reduced ankle motion resulted in less power output in FIG. 12. The performance of the orthosis could be improved with more advanced torque-based control algorithms, e.g., potential energy shaping control.

Figure 13:
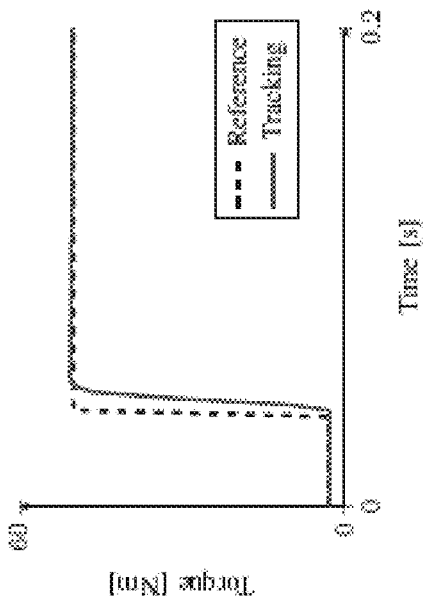
FIG. 13 illustrates results from a static high torque in accordance with one embodiment.

To verify the actuator's peak output torque, as well as its response time, a high torque step response test was conducted. The actuator was mounted to the test platform, and its output shaft was mechanically fixed. Then, a low torque of 3 Nm was set to preload the actuator and minimize the influence of mechanical backlash. Finally, a torque of 50 Nm was commanded, maintained for 5 seconds, and then set back to zero. We tested with 50 Nm to avoid potential overload of our actuator during dynamic test. The results of this test are plotted in FIG. 13. Once the system had settled, the steady-state error was less than 1.3%. These test results were imported into MATLAB Control and Simulation Toolbox, and were used to generate a model of the system. This model suggests that the system's torque bandwidth frequency is 10 Hz, which greatly exceeds the required bandwidth for human walking (1-2 Hz).

Figure 14:
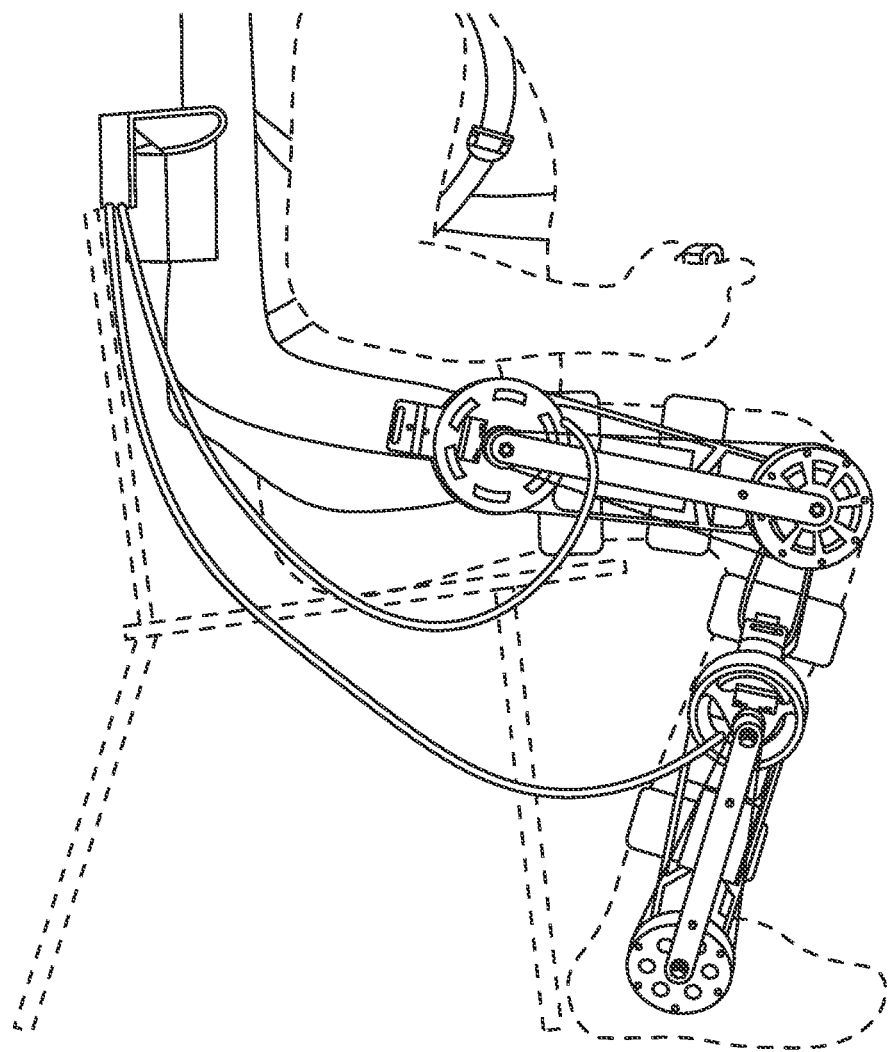
FIG. 14 illustrates a sit-to-stand test in accordance with one embodiment.
Figure 15:
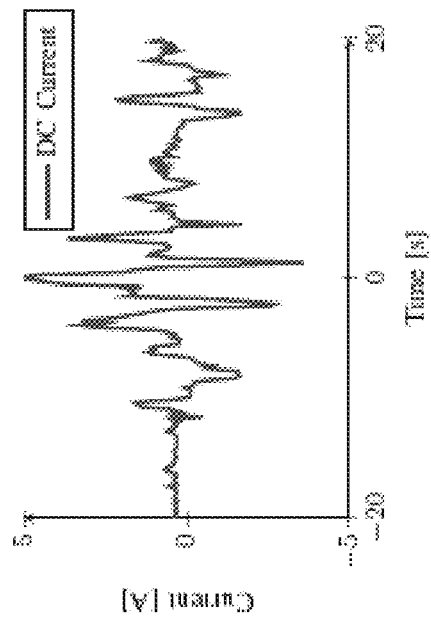
FIG. 15 illustrates measured DC-link current from regeneration test in accordance with one embodiment.

The regeneration test is implemented to verify the energy harvesting function of the presented orthosis. We choose to test the regeneration capability though a sit-to-stand experiment. A human subject wearing the presented orthosis was asked to stand up from chair and sit back down, a sit-to-stand cycle. We repeat this cycle 8 times within 40 seconds. The experiment environment is shown as FIG. 14. During the whole experiment, the DC-link current of the power supply was recorded. The measured DC-link current is shown in FIG. 15. From the measured current data, the system can harvest the negative energy from human motion during sitting. The average harvested energy of 8 sit-to-stand cycles is about −23.91 J.

The present disclosure has designed and validated a light-weight, mobile, powered knee-ankle orthosis for gait rehabilitation training. As the designed orthosis has a torque dense motor and a low-ratio transmission, intrinsic backdrivability and high torque and power output may be achieved with a simple structure. At the same time, the presented orthosis can maintain and track a high torque output at a high walking speed. Accordingly, an orthosis manufactured in accordance with this disclosure is a suitable platform for testing different rehabilitation control strategies.

Moreover, since the actuator is nearly a direct drive system, it demonstrates several advantages, such as improved dynamic performance, reduced intrinsic backdrive torque, and an almost linear torque constant. If intrinsic backdrive torque can be further decreased in the design, it will be possible to control the actuator's output torque with motor current feedback instead of torque sensor feedback. This would allow the cost and weight of the torque sensors to be removed from the orthosis design.

The present disclosure may additionally benefit from the implementation of more advanced torque control algorithms and performing experiments with patient subjects. Additionally, a battery system with regenerative power electronics may also be added to the back brace for untethered operation of the orthosis.

Those skilled in the art to which this application relates will appreciate that other and further additions, deletions, substitutions and modifications may be made to the described embodiments.

What is claimed is:

1. An orthosis device, comprising:
   an actuator housing;
   an electric motor coupled to the actuator housing, the electric motor including a motor stator and a motor rotor, the electric motor having a torque density of at least 3.3 Nm/kg; and
   a low-ratio transmission coupled to the actuator housing, the transmission including:
   a gear system coupled to the actuator housing; and
   a drive system coupling the electric motor and the gear system, wherein a combination of the electric motor and transmission provide a user backdrivable orthosis device, wherein one of the actuator housing or an output of the low-ratio transmission is configured to couple to one or more bones on one side of a joint of a user, and the other of the output of the low-ratio transmission or the actuator housing is configured to couple to one or more different bones on an opposing side of the joint of the user.

2. The orthosis device of claim 1, wherein the electric motor has a very high output torque.

3. The orthosis device of claim 1, wherein the electric motor has an extremely high output torque.

4. The orthosis device of claim 1, wherein the electric motor is a permanent magnetic synchronous motor.

5. The orthosis device of claim 1, wherein the transmission is a very low-ratio transmission.

6. The orthosis device of claim 1, wherein the transmission is an extremely low-ratio transmission.

7. The orthosis device of claim 1, wherein the gear system is a planetary gear system.

8. The orthosis device of claim 7, wherein the planetary gear system has a single sun gear, three planetary gears and a single ring gear.

9. The orthosis device of claim 8, wherein the transmission is a two-stage transmission.

10. The orthosis device of claim 8, wherein the transmission is a very low-ratio transmission.

11. The orthosis device of claim 1, wherein the drive system includes a timing belt coupling the electric motor and the gear system, and further wherein the timing belt is at least 80% efficient.

12. The orthosis device of claim 1, wherein the gear system is located within a driven sprocket of the orthosis device.

13. The orthosis device of claim 1, wherein the stator at least partially surrounds the rotor.

14. The orthosis device of claim 1, further including a motor encoder associated with the electric motor.

15. The orthosis device of claim 1, further including an actuator driver coupled to the actuator housing, the actuator driver configured to control the electric motor.

16. An orthosis device, comprising:
   an actuator housing;
   an electric motor coupled to the actuator housing, the electric motor including a motor stator and a motor rotor, and the electric motor further having high output torque; and
   a very-low ratio transmission coupled to the housing, the transmission including:
      a planetary gear system coupled to the housing; and
      a drive system including a timing belt coupling the electric motor and the planetary gear system, wherein a combination of the electric motor and transmission provide an extremely user backdrivable orthosis device.

17. The orthosis device of claim 16, wherein the electric motor is a frameless electric motor.

18. The orthosis device of claim 16, wherein the actuator housing, electric motor, planetary gear system, and drive system are a first actuator housing, first electric motor, first planetary gear system, and first drive system of a first movable portion of the orthosis device, and further including a second actuator housing, second electric motor, second planetary gear system, and second drive system of a second related movable portion of the orthosis device.

19. The orthosis device of claim 18, wherein the first movable portion is configured to assist with movement of a user's knee, and the second related movable portion is configured to assist with movement of the user's ankle.

20. The orthosis device of claim 16, wherein the actuator housing, electric motor and transmission weigh less than 2 kg.

* * * * *